(12) United States Patent
Krigmont

(10) Patent No.: US 11,484,619 B2
(45) Date of Patent: Nov. 1, 2022

(54) MULTI STAGE DISINFECTING AIR CLEANER

(71) Applicant: Henry Krigmont, Seal Beach, CA (US)

(72) Inventor: Henry Krigmont, Seal Beach, CA (US)

( * ) Notice: Subject to any disclaimer, the term of this patent is extended or adjusted under 35 U.S.C. 154(b) by 0 days.

(21) Appl. No.: 17/025,010

(22) Filed: Sep. 18, 2020

(65) Prior Publication Data
US 2022/0088260 A1    Mar. 24, 2022

(51) Int. Cl.
| | | |
|---|---|---|
| *A61L 9/20* | (2006.01) | |
| *A61L 9/22* | (2006.01) | |
| *A61L 9/014* | (2006.01) | |
| *F24F 8/22* | (2021.01) | |
| *F24F 8/30* | (2021.01) | |
| *F24F 8/158* | (2021.01) | |
| *A61L 9/03* | (2006.01) | |
| *A61L 9/015* | (2006.01) | |

(52) U.S. Cl.
CPC ................ *A61L 9/20* (2013.01); *A61L 9/014* (2013.01); *A61L 9/015* (2013.01); *A61L 9/032* (2013.01); *A61L 9/22* (2013.01); *F24F 8/158* (2021.01); *F24F 8/22* (2021.01); *F24F 8/30* (2021.01); *A61L 2209/22* (2013.01); *F24F 2221/125* (2013.01)

(58) Field of Classification Search
CPC . A61L 9/032; A61L 9/015; A61L 9/20; A61L 9/22; F24F 8/22; F24F 8/30
See application file for complete search history.

(56) References Cited

U.S. PATENT DOCUMENTS

| | | | | | |
|---|---|---|---|---|---|
| 5,855,653 | A | * | 1/1999 | Yamamoto | ............. B03C 3/155 |
| | | | | | 96/58 |
| 5,879,435 | A | * | 3/1999 | Satyapal | ............... F24F 1/0076 |
| | | | | | 96/16 |
| 10,933,158 | B2 | * | 3/2021 | Benedek | ............. B01D 53/869 |

\* cited by examiner

*Primary Examiner* — Robert A Hopkins
(74) *Attorney, Agent, or Firm* — Clifford H. Kraft

(57) ABSTRACT

A portable air filtration apparatus capable of rapid and efficient room air turnover and recirculation of filtered and decontaminated air with eradication of both microorganisms and biological agents. The invention relates to a compact device that can be used in ultra-clean air purification using a multi stage electrostatic precipitation and air filtration with disinfection and eradication of both microorganisms and biological agents by the application of ultraviolet light radiation. It can be used in any application where space, lower cost or ultra-fine particulate filtering is needed; such as in clean rooms and surgical suites. The device is extremely efficient for purifying contaminated air from entrained dust and organic substances without using chemicals and physical filters, and it is hygienic and fireproof. The device including its multi stage electrostatic precipitator with the filter, connecting, releasing tubes and the fan is easy to clean and can be portable.

18 Claims, 6 Drawing Sheets

Multi Stage Disinfecting Air Cleaner: Corona Discharge

Multi Stage Disinfecting Air Cleaner: Barrier Filter Operation

MULTI STAGE DISINFECTING AIR CLEANER

BACKGROUND

Field of the Invention

The invention concerns a procedure for removal and destruction of organic substances in contaminated air. More specifically, the present invention relates to a method and a portable filter for capturing airborne dust and other agents, such as microorganisms, including viruses, pathogens, and microbial antigens, as well as toxins and allergens and other harmful contaminants.

Description of the Problem Solved

Air in private houses, professional offices, commercial buildings, hospitals, laboratories, correctional facilities or special service environments frequently contains not only airborne dust particles, but also bacteria and microorganisms that spread disease. An increasing problem of airborne microorganisms, including viruses (e.g. influenza, SARS, MERS, CONVID-19, etc.), as well as of microbial and other antigens and toxins, resulting in increased morbidity and mortality due to aggressive viruses, resistant bacteria and sensitivity to allergens and toxins, requires an efficient method to remove these agents and molecules from contaminated air of various environments and premises.

Such microorganisms cause infectious diseases like pneumonia, influenza, tuberculosis (TB), herpes and hepatitis B, SARA, CONVID-19, and the common cold. When a person coughs, sneezes or speaks, he/she expels airborne particles or "droplet nuclei." If the person expelling has contracted an infectious disease, such as tuberculosis, these droplet nuclei may contain TB bacteria, which then can become aerosolized as droplets.

Similarly, if a person expelling has contracted CONVID-19, these droplets nuclei would contain CONVID-19 viruses, thus another person inhaling can become in turn infected and contagious with the decease.

The World Health Organization (WHO) and Centers for Disease Control and Prevention (CDC) postulate that the particles of more than 5 µm as droplets, and those less than 5 µm, as aerosols are droplet nuclei. Conversely, there have been some other postulations, indicating that an aerodynamic diameter of 20 µm or 10 µm or less should be reckoned to be aerosols based on their ability to linger in the air for a prolonged period, and the reachability to the respirable fraction of the lung (alveolar region). Small aerosols are more susceptible to be inhaled deep into the lung which causes infection in the alveolar tissues of the lower respiratory tract, while large droplets are typically trapped in the upper airways. Thus, aerosols can be defined as suspensions of solid or liquid particles in the air which can be generated by either natural or anthropogenic phenomena.

Droplet transmission occurs by the direct spray of large droplets onto conjunctiva or mucous membranes of a susceptible host when an infected patient sneezes, talks, or coughs. Droplet nuclei can remain airborne for long periods, up to hours, which increases the possibility they can be inhaled by another person. Anyone breathing air contaminated in this manner can become infected. Stable droplet nuclei can range from 1 to 4 microns in size. For example, the well-studied individual tuberculosis bacilli are rod shaped and can vary in width from 0.2 to 0.6 microns, and from 0.5 to 4.0 microns in length. Any concentration of aerosolized droplet nuclei containing tubercle bacilli is assumed to provide some infection risk. Health care workers providing clinical and diagnostic procedures, examinations and autopsy activities are at greater risk due to the nature of their services.

Table 1

Detailed information of droplets and aerosols generated from human expiatory activities

TABLE 1

Detailed information of droplets and aerosols generated from human expiratory activities

| Activity | Number of droplets and aerosols generated (1-100 µm) | Presence of aerosols (1-2 µm) | Region of origin |
| --- | --- | --- | --- |
| Normal breathing (for 5 min) | None-few | Some | Nose |
| Single strong nasal expiration | Few hundred | Some | Nose |
| Counting loudly - talking | Few dozen- few hundred | Mostly | Front of mouth |
| A single cough (mouth open) | None-few hundred | Some | Faucial region |
| A single cough (Mouth initially closed) | Few hundred- many thousand | Mostly | Front of mouth |
| Simple sneeze | Few hundred thousand-Few million | Mostly | Front of mouth |
| | Few-few thousand | Some | Both nose and Faucial region |

Table 1 above yields and estimate of the number of droplet nuclei expelled by breathing, coughing and sneezing.

The SARS-CoV-2 virus has been found to remain viable in aerosols for 3 hr, while it, in the form of droplets is more stable on plastic and stainless steel or copper, cardboard and glass with durations detected up to 72, 4, 24 and 84 hr, respectively. In comparison, the SARS-CoV virus was also found to be airborne in the form of aerosols for 3 he, indicating that both SARS viruses behave more or less in the same manner in the air. Nevertheless, the SARS-CoV virus remains stable and viable in the form of droplets on plastic and stainless steel or copper, cardboard, and glass with durations (half-lives) lasting to 72, 8, 8, and 96 hr, respectively. The half-lives of the SARS-CoV-2 and SARS-CoV are almost the same in aerosols, with median estimates of approximately 1.1-1.2 hr, indicating that both viruses have similar stability characteristics in transmitting through the. However, the more profound epidemiological sustenance of the SARS-CoV-2 virus may, therefore, be because of some other factors, including high viral loads in the upper respiratory tract and the capability of persons infected with COVID-19 to shed and transmit the virus while remaining asymptomatic.

In addition, it has been estimated that particles emitted from a cough of an infected person of a respiratory illness quickly decrease in diameter (with initial diameters of less than 20 µm) mainly because of the water loss by approximately half of the initial volume, amounting to $6 \times 10^{-8}$ mL. Exhaust ventilation, particle settling, die-off, and air disinfection methods are some prominent mechanisms by which the removal of viable airborne pathogens often takes place; each removal mechanism follows a first-order reduction rate. Based on 3-h viability of SARS-CoV-2 in the air, prerequisites for the disease such as exposure, inhalation, and infection could occur minutes or a few hours later near and far from an aerosol source even in a stagnant environment.

Private residences. outpatient clinics, emergency rooms, correctional facilities, homeless shelters and other locations of first contact with an infected person are places of particular concern. It therefore would be very desirable to be able to filter the air in these high-risk areas to remove airborne infections materials as far as possible to diminish the risk of infection to those exposed in such high-risk areas.

The latter include environments with conventional air filters, such as hospital operating theatres and hospital ward rooms, e.g. ward rooms for severely immune-suppressed patients.

In modern hospitals, an increasing number of patients are receiving immunosuppressive therapy for cancer and other serious diseases making them highly sensitive to a variety of infectious agents, while patients who have been struck by highly contagious agents are treated in infectious disease isolation wards that are commonly situated within the same hospital buildings. Also, other environments where presently no air filters are in common use, including day care centers, kindergartens and schools, especially for small children, air-borne microorganisms (e.g. penicillin-resistant pneumococci causing middle ear inflammation and pneumonia) may pose a threat, and such environments would thus benefit from air-cleaning measures.

Furthermore, premises used in the globally fast-growing poultry industry and other food production require efficient removal of viruses and bacteria from air to reduce the risk of microbial contamination and exchange of organisms that may undergo genetic recombination potentially resulting in epidemic outbreaks of serious infections, such as the bird and swine flu. Also, in transportation vehicles, including airplanes, conventional air conditioning equipment may carry microorganisms from one infected passenger to other passengers.

Although isolation rooms for patients with infectious diseases are available, such rooms are generally specially designed, or at least structurally retrofitted, to provide a negative pressure isolation room using central ventilation system equipment. In connection with such isolation rooms, as well as hospital and industry clean rooms, high efficiency particulate air or HEPA filters or ultra-low penetration air or ULPA filters have been used to filter the air, which is exhausted from the room through ceiling ducts.

Furthermore, when an air stream passes through an HEPA or ULPA filter, there is a significant added pressure drop. Central plant central station fan equipment may not be able to overcome the added pressure drop created by these filters. Although with new construction, fan equipment can be added for specific rooms that are wanted for isolation purposes, with older structures this would require significant and expensive construction involving tearing down and rebuilding ceilings and possibly walls, and additional wiring, to put the additional fans within the exhaust system Moreover, conventional mesh network air filters have limited capacity to capture small bacteria, viruses and components of microorganisms, as well as molecules like allergens and toxins. The most advanced conventional filter system is the High Efficiency Particulate Air (HEPA) filter which is preferably used for cleaning the air in high risk laboratories. One disadvantage with mesh network filters is their inherent inability to kill infectious agents that may have been caught by the filter. Another disadvantage is that they get clogged and become inefficient after variable periods of time and then can potentially start leaking because of the high air pressure that is then required to overcome the filter resistance. Notably, bound infectious microorganisms may then detach and pose a risk to individuals in the environment.

The unique ability of the proposed electrostatic barrier filter apparatus to collect the smallest micron-sized aerosol droplets, allows the MSDAC to draw the air in at the "breezing" level, thus, in fact, offering a first-line protection for the room inhabitants from aerosolized suspended particles. The finest airborne droplets would be eventually drawn into the MSDAC device and destroyed.

Today there are patents or patent applications on conventional filters based on mesh networks with the capacity to clean the air from microorganisms, including patent applications based on capturing microorganisms by electrostatic binding. The above-mentioned drawback with mesh network filters, including HEPA-filters, with their gradual clogging leads to increasing air resistance and decreasing filtering efficiency over time. These insufficiencies, which are difficult to detect and control, pose a risk despite the fact HEPA-filters are usually regularly exchanged over time. Moreover, the exchange procedure of mesh network filters, including HEPA-filters, is in itself connected with a certain risk of spreading infectious microorganisms stuck in the filter. Finally, HEPA filters are generally expensive and require efficient pre-filtering systems.

Since increasing of the air traffic between countries and continents this mode of transmission of microorganisms will have to be taken seriously. Finally, the global climate changes that are thought to take place will most likely affect the disease panorama in many parts of the world and, among other things, result in increased demand for efficient removal of viruses and other microorganisms, as well as allergens and toxins, from air.

Accordingly, there is an increasing need for a new technique for taking care of the problems with airborne harmful agents.

SUMMARY OF THE INVENTION

The present invention includes a compact, portable air filtration apparatus capable of rapid and efficient room air turnover and recirculation of a filtered and decontaminated air. The present invention can be used in ultra-clean air purification by the method of a multi stage electrostatic precipitation and air filtration with disinfection and eradication of both microorganisms and biological agents, by the application of ultraviolet light, x-ray or radiation, in any application where space, lower cost or sub-micron and nano-particulate filtering is needed; such as in clean rooms and surgical suites.

The Multi Stage Disinfection Air Cleaning (MSDAC) apparatus of the present invention includes a generally rectangular or circular housing sized to accommodate the required air cleaning and germicidal equipment within the housing which includes mounting for an electrostatic and mechanical air filter, a germicidal chamber, and a fan assembly. An opening is provided in the housing for exhausting air drawn by the fan through the intake opening and the electrostatic air filter, and out of the exhaust opening. The apparatus can be additionally provided with an optional germicidal ultra-violet lighting element either between the electrostatic air filter and fan or upstream of the electrostatic air filter to provide added decontamination of the filter within the housing or plenum, and with a speed control device to adjust the speed of air flow through the unit.

Contaminated air is charged, filtered and cleaned both electrostatically and mechanically and the air stream can be radiated with ultra-violet light. Embodiments of the present invention kill the captured microorganisms, including viruses, and inactivate captured antigens, toxins and allergens.

The invention also includes a filter device for removing and/or destroying organic substances in contaminated air, which comprised of an enclosed room or a housing and at least one ventilator for sending the air stream through the enclosure, in which there, in open connection with each other, are: a first zone with an opening, which is connected to a source of contaminated air, a second zone where a gas flow can be immediately exposed to a high-tension corona discharge electric field which results in a strong ionic flow; thus charging and collecting the incoming effluent. Subsequently, the charged flow enters a third zone containing a high-tension uniform electric field that causes the charged particles to migrate to one of the charged electrodes. One of the electrodes can be made of porous conducting filter material that allows the cleaned gas to flow into the fourth zone while filtering the remaining effluent that is collected prior to the ultra-clean gas being directed into a fifth (germicidal) zone which contains a number of UV lamps for irradiating the air current with ultra-violet light with a volume allowing the air current, at predetermined interval of time, to stay in the germicidal zone, and which has an opening through which the purified air is released to the surroundings.

Alternate embodiments can include a sixth zone containing a chamber with a charcoal filter to eliminate the ozone from the clean exhaust, and which has an opening, through which the purified air passes in order to be released to the ambient surroundings. In addition, a variety of locations of the germicidal zone with respect to the multi stage air filtering stage are possible.

It is an object of the present invention to provide a method and an apparatus for capturing airborne agents which solves the problems associated with the prior art and meets future demands of capturing airborne microorganisms.

Another object of the present invention is to provide a Multi Stage Disinfecting Air Cleaner which is adapted to remove or neutralize virus contagions present in the surrounding ambient air and thereby reduce the risk to the inhabitants of exposure to or infection from airborne chemical, bacterial and other contaminants, thereby contributing to the public health and wellbeing.

Another object of the present invention is to provide a Multi Stage Disinfecting Air Cleaner which is adapted to remove virtually all particulate and dust airborne contaminants using the multistage air cleaning combining the electrostatic precipitator and mechanical filtration.

Another objective of the present invention is to provide a MSDAC which is easy to carry by hand and which can be easily installed to and removed from a variety of typical private and commercial properties.

Another object of the present invention is to provide a Multi Stage Disinfecting Air Cleaner which in preferred embodiments is operable from the external electrical system such as to allow for the use of higher wattage UVC germicidal lamps.

Another object of the present invention is to provide a Multi Stage Disinfecting Air Cleaner in certain embodiments which can operate on battery power alone for a reasonable amount of time.

Another object of the present invention is to provide a Multi Stage Disinfecting Air Cleaner which is adapted to be powered from conventional alkaline batteries.

Another object of the present invention is to provide a MSDAC which is adapted to be powered by rechargeable batteries.

Another object of the present invention is to provide a Multi Stage Disinfecting Air Cleaner which utilizes a unique design to reduce cost, weight, size and operating costs while delivering a superior air cleaning performance.

Another object of the present invention is to provide a Disinfecting Air Cleaner which provides radio frequency shielding around the inverter, charging and precipitator plates so as to reduce any chance of generated radio frequency interference.

Another object of the present invention is to provide a Disinfecting Air Cleaner having a corona discharge and precipitator collection system for killing pathogens, detoxifying chemical pollutants, and electrostatic capture of undesirable particulates in the air stream.

Another object of the present invention is to provide a Disinfecting Air Cleaner which incorporates a user replaceable activated carbon after filter to remove or degrade any odors still present in the air stream after the ducted air stream passes through the Disinfecting Air Cleaner section of the purifier.

It is another object of the present invention to provide a Disinfecting Air Cleaner which provides a replaceable activated carbon filter to remove generated ozone from the air stream.

Another object of the present invention is to provide a Disinfecting Air Cleaner that operates quietly and has no moving parts except a fan.

Another object of the present invention is to provide a Disinfecting Air Cleaner that contributes to the health and safety of the public.

These and other objects of the invention made herein will become readily apparent upon further review of the following specification and associated drawings.

DESCRIPTION OF THE FIGURES

Attention is now directed to several figures that illustrate features of the present invention.

Several illustrations have been provided to aid in understanding the present invention. The scope of the present invention is not limited to what is shown in the figures.

DESCRIPTION OF THE PREFERRED EMBODIMENTS

Figure 1:
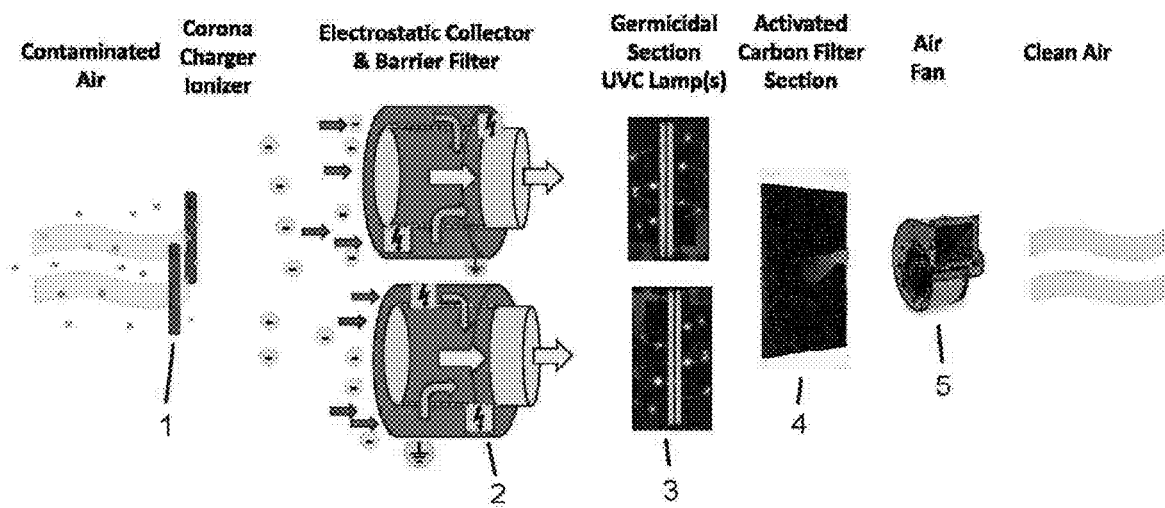
FIG. 1 shows a stage-by-stage representation of an embodiment of the present invention.
Figure 2:
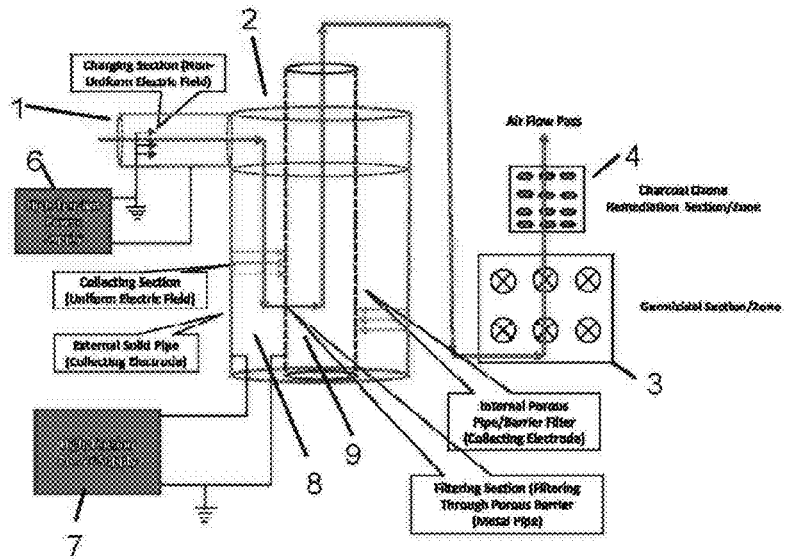
FIG. 2 is a schematic diagram of the embodiment of FIG. 1.

FIG. 1 shows a side-by-side layout of an embodiment of the present invention. The invention relates to a filter device for removing and/or destroying organic substances in contaminated air. Embodiments comprise a housing and at least one ventilator or fan for sending an air stream through the housing. There are, in open connection with each other, a first zone with an opening which is connected to a source of contaminated air; a second zone 1 where the airflow can be immediately exposed to a high-tension corona discharge electric field which results in a strong ionic flow thus charging and collecting the incoming effluent. Subsequently, the charged flow enters a third zone 2 containing a high-tension uniform electric field that causes the charged particles to migrate to one of the oppositely charged electrodes. One of the electrodes can be made of porous filter material such as sinter metal, sinter stainless steel or other porous conducting material that allows the cleaned gas to flow into a fourth zone while filtering the remaining effluent that is collected prior to the ultra-clean gas being directed into a forth zone 3 with a number of lamps for radiating the air current with ultra-violet light. This zone has a volume allowing it to contain the air current for a predetermined interval of time, and includes an opening through which the purified air may be released to the ambient. An optional activated charcoal filter 4 and follow the fourth zone, or the air can be directly returned by the ambient after the fourth zone. A fan or ventilator 5 moves the air through the system.

After entering through the inlet opening (first zone) the air moves into the second zone of the housing. The air first passes through one or more ionizing wires or charging points 1. The wires are energized at a relatively high voltage of several thousand volts. There the ionizing wires impart an electrical charge on the molecules air flow (second zone), creating charged molecules known as ions, some of which eventually cling to airborne particles. Additionally, a corona created on the ionizing wires generates ozone which is capable of chemically reacting with organic molecules so as to break down organic contaminants, this in addition to the germicidal action of the subsequent UVC lamp can kill pathogens. The air flow next encounters the third stage of the electrostatic precipitator 2 or series of concentric particle collection tubes 8, 9, which are energized in a bi-polar fashion, separately from the ionizing wires thus creating a uniform high-tension electrostatic field. The charged concentric collection tubes attract the charged particles from the air stream, and due to the static charge thereon from the power source, deposits the particles removed from the air stream onto the concentric precipitator tubes.

One of the electrodes 9 can be made of porous filter material that allows the cleaned gas to flow into the fourth zone while filtering the remaining effluent that is collected prior to the ultra-clean air being directed into a fourth zone 4 with a number of lamps for radiating the airflow with ultra-violet light with a volume allowing the airflow, at predetermined interval of time, to stay in the zone, and which has an opening through which the purified air is released to the ambient or put through an optional activated charcoal filter.

The ionizing and precipitator plates are energized by power sources 6, 7 contained in a separate portion of the Disinfecting Air Cleaner housing. Typically, the power sources may be located in a base portion directly under or next to the electrostatic filter portion. In other embodiments the power source may be located in a location where space and electrical wire routing best permits. An inverter converts a relatively low voltage to the high voltage required to drive the ionizing wires and electrostatic precipitator pipes. The lower voltage supply may be a 115-volt alternating current supply, or other voltage supply as available. Other embodiments can be powered by self-contained batteries, either rechargeable or disposable varieties. The power consumption of the ionic wires and the precipitator is quite low making the powering of the invention from batteries feasible. Depending on the type of germicidal lamp used, the largest consumer of electrical energy in the device can be the germicidal UVC lamp. For example, for illustration, using a commonly available germicidal mercury arc UVC GTL3 series miniature lamp having an ANSI standard E17 base lamp powered at 10 volts, the lamp consumes 3 watts, or about 300 mA at 10 volts. In the case of battery powered embodiments, for lower power consumption, the UVC lamp can be switched off if desired, although its use is highly desirable. The power consumption of the UVC germicidal lamp is a motivator for the use of an externally powered arrangement.

As discussed previously, one of the concentric electrodes can be made of porous filter material that allows the cleaned gas to flow into the next zone while filtering the remaining effluent that is collected prior to the ultra-clean gas being directed into a zone with a number of UV-C lamps for radiating the air current with ultra-violet light. This zone has a volume allowing it to contain the air current for a predetermined interval of time, and includes an opening through which the purified air is released to the ambient.

In other words, prior to exiting the Disinfecting Air Cleaner, the air encounters the germicidal section having an ultraviolet (UV) lamp which emits short wavelength UV light in the germicidal spectrum (UVC). For highest germicidal efficiency the UVC light source should emit at around 222 to 270 nm wavelength. The air duct region surrounding the UVC light source is provided with a UVC reflective material to multiply by reflection the germicidal effect of the UV lamp emissions. As stated, particular embodiments of the subject air purifier are battery operated, and in such battery-operated embodiments, the UVC lamp is necessarily of limited wattage so as to conserve battery life and limit the space requirements for the UVC lamp. In such battery powered embodiments, the use of reflective materials in the germicidal portion of the Disinfecting Air Cleaner are especially beneficial. It is seen as preferable that the Disinfecting Air Cleaner be powered from an external power supply since the battery operation has its limits on the use of higher wattage and therefore higher UVC intensity germicidal lamps.

Air flow leaving the germicidal portion then enters the ozone filter portion of the housing. The apparatus can be equipped with an activated charcoal filter to help remove odors that may have made it past the ionic purifier as well as to remove ozone. Ozone is produced by all ionic air purifiers as a byproduct to the air ionization process. Ozone in significant concentrations is an irritant to the human body, and it is desirable to reduce its presence in the outlet air stream of the purifier. A limitation of conventional ionic purifiers is that they do not provide a means of removing ozone from the outlet air stream. In the air purifier of the present invention, the purifier is provided with a replaceable activated charcoal filter located after the electrostatic and germicidal purifier portion of the housing. Activated charcoal has been tested and shown to be very effective in removing ozone from an air stream directed through the filter.

An article as published in the American Industrial Hygiene Association Journal of September, October 1999, summarizes the results of a study at the University of Minnesota on the removal of ozone using activated carbon filters. The findings include the following quotation "Activated carbon filters can be very effective at ozone removal, although not indefinitely because chemical reactions of ozone and carbon change the carbon." Therefore the addition of a user replaceable activated carbon filter following the ionic purifier can be advantageous in two ways, first by absorbing additional odors and chemicals from the air stream that may have made it past the ionic purifier, and secondly by removing ozone created in the ionic purifier from the air stream and thereby preventing the addition of another chemical irritant to the air.

The Multi Stage Disinfecting Air Cleaner according to the present invention is designed to operate quietly as it has no moving parts except of the fan, and relies upon the forced air flow through the "tail" air vents to provide the motive force to drive the air through the device.

By means of this construction, the procedure according to the invention can be carried through efficiently and economically. The respective zones are following each other with the fifth zone being the last. The air current, which is generated by the fan, is then successively passing the various zones and thereby run through the processes which finally result in purified and decontaminated air being released into the environment.

The fan can in principle be inserted any place at all in the air current, but it is most expedient to place the fan after the exit zone and connect its opening with the suction side of the ventilator.

The air passing through the fan is thereby purified and decontaminated air only, which prevents the build-up of a coating of organic substances from contaminated air in the fan, which would reduce the efficiency of the fan.

From the source of contamination, the contaminated air streams into the first zone via its inlet. Since it may be more than a single gas passage required to accommodate the overall gas flow, it is important that the air is distributed equally in the parallel channels for the processes to run at their optimum. For this purpose, according to the invention, there can advantageously be placed one or more distribution plates in the first zone, preferably somewhere behind the inlet opening of the air.

Filtered and purified air flows then into the outlet portion of the housing where it flows through diffusers and out into the surrounding ambient of the Disinfecting Air Cleaner.

Figure 3:
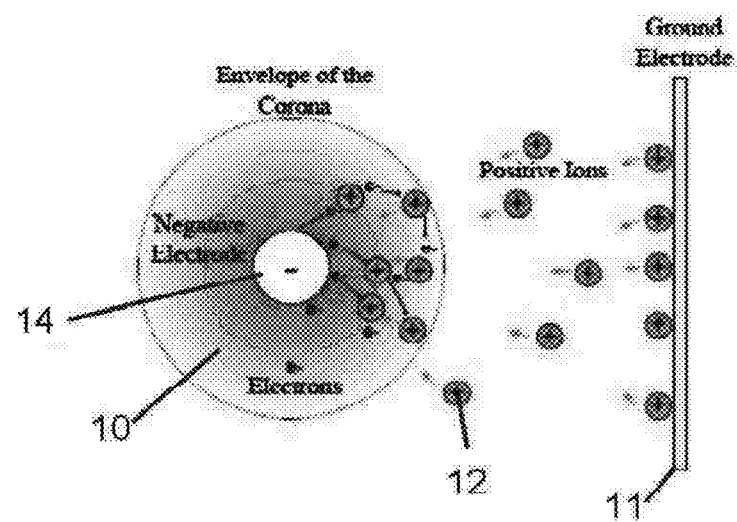
FIG. 3 shows a corona discharge mechanism.

FIG. 3 shows details of a corona discharge section. An ionizing electrode 14 creates a corona 10 that forms ions 12 that are attracted to a ground electrode 11. The ionizing electrode is usually negative; however, a reversed system will also work with the center electrode positive. Either configuration is within the scope of the present invention.

Figure 4:
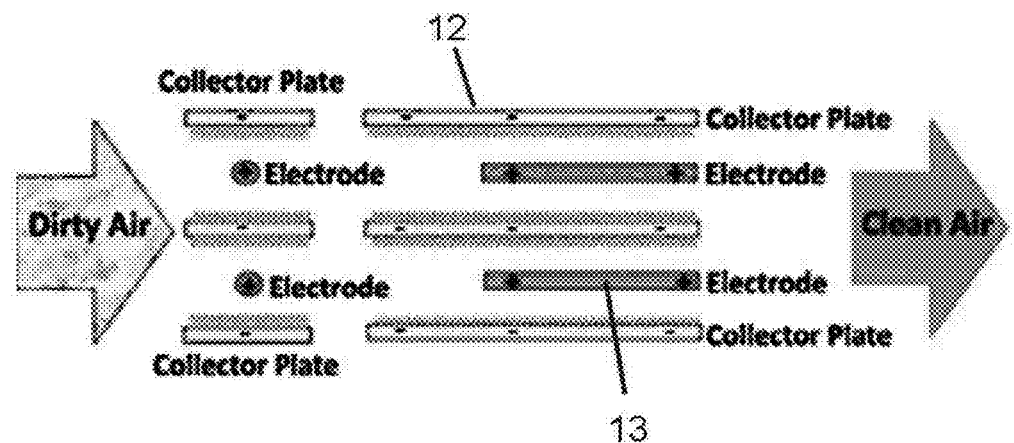
FIG. 4 shows an arrangement of electrodes in an electrostatic precipitator.

FIG. 4 shows a corona discharge section in tandem with a set of linear field electrodes 12, 13. This embodiment of an electrostatic precipitator simply passes the air through a passage. There is no bag or porous filter in this embodiment.

Figure 5:
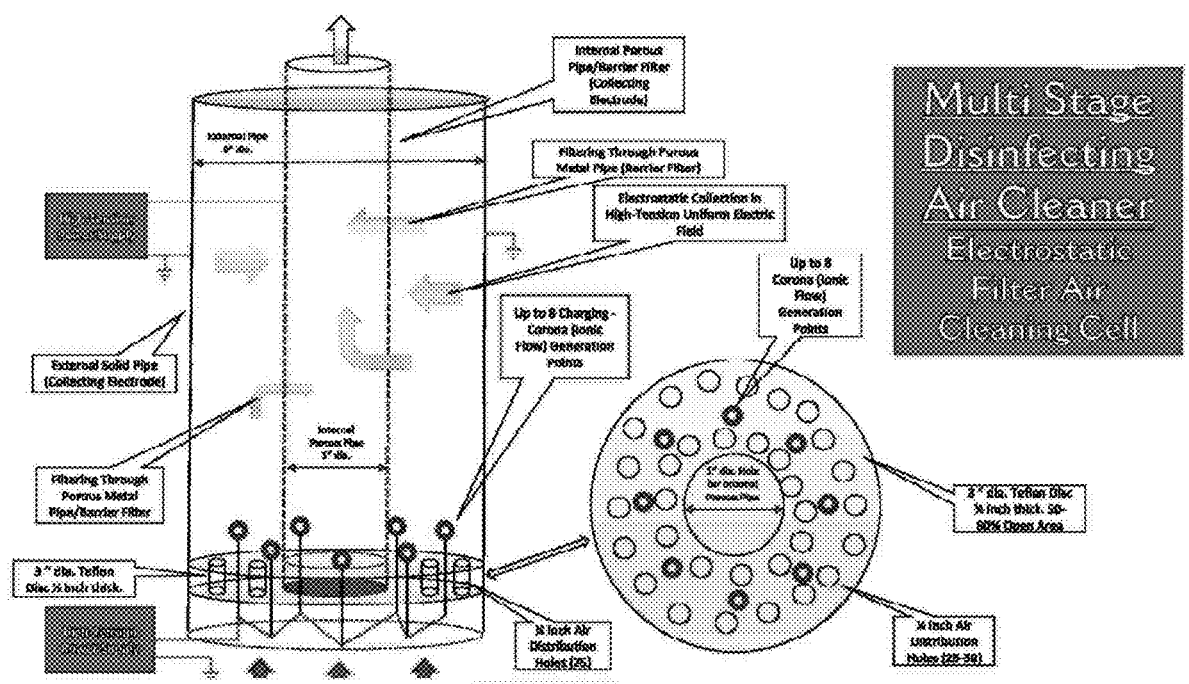
FIG. 5 shows details of an electrostatic cleaning cell.
Figure 6:
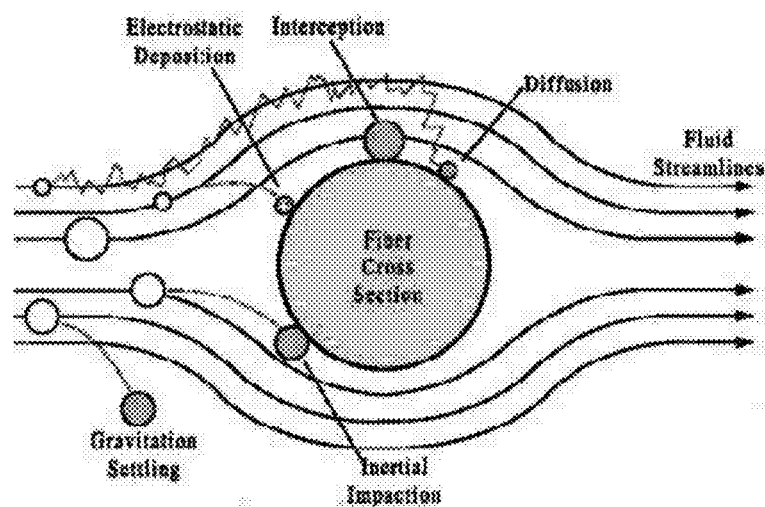
FIG. 6 shows details of a barrier filter.

FIG. 5 shows details of an electrostatic cleaning cell with a porous filter in the center. FIG. 6 shows details of the operation of a porous pass-through filter.

In a second embodiment of the Multi Stage Disinfecting Air Cleaner particularly suited to low power operation from self-contained batteries, the mercury arc UVC lamp is replaced with one or more ultraviolet UVC spectrum rated light-emitting diodes (LEDs). The LEDs consume nominally 20 mA each up to 50 mA each for the 'superflux' LED varieties and so greatly reduce the power drain compared to the GTL3 series or larger more effective UVC lamps.

In a third series of embodiments of the present invention, the Multi Stage Disinfecting Air Cleaner is provided with means of connecting an external power source, eliminating the need for batteries internal to the air purifier housing. Embodiments of the externally powered MSDAC are well supplied with the power to utilize higher wattage UVC lamps such as available UVC rated mercury arc lamps to provide potent germicidal irradiation of the ducted ambient air.

Thus, the air purification system of the invention is portable and extremely easy to use. All that an operator need do is to wheel it into a room and plug it into an electrical receptacle. The resident can benefit from clean, purified air immediately. Further, embodiments of the invention can be equipped with a set of directional vanes designed to set up the correct air patterns.

The clean, purified air is most effectively directed upwards, across the ceiling, and drops down around the total room area via the walls, pushing any dust, pollen or odors toward the floor and back into the unit. While the unit of the invention is effective wherever it is placed within the room, its placement is recommended at a wall opposite the region in which the clean air benefits are most desired.

Industry guidelines suggest four (4) to six (6) air changes (turnovers) per hour (ACH) for adequate airborne cleaning and allergy control. Particular embodiments of the system of the present invention will change up to 393 cfm (667 $m^3$/hr), or as high or higher than 400 cfm.

The upward air discharge provided by the system of the invention more completely mixes the air in a room by using the ceiling and upper spaces of the room to completely distribute the air to all areas. When air flow patterns move across the ceiling and upper spaces, there is no obstruction for the air getting back to the Disinfecting Air Cleaner unit. When there is no obstruction, the mixing of all the air is more complete, and therefore, the filter unit is more effective with less drafts than prior art side, bottom or front air discharge type units seen on the market today. This top discharge allows higher air flow rates to better clean the air rapidly with complete mixing, resulting in cleaner and purer air to breathe throughout the room.

As can be appreciated, the size or capacity of the fan assembly depends on the size of the housing and the size of the room in which air purification is desired, and the extent of purification needed. The American Society of Heating, Refrigeration and Air Conditioning Engineers or ASHRAE has published recommendations for ventilation in Tuberculosis (AFB) isolation rooms. Clearly, the most current experience with the COVID-19 pandemic had taught that the requirement dictated by the COVID-19 requirements should be at least as stringent as ones described herein. These recommendations specify that such rooms should have at least four (4) to six (6) total air changes per hour, including at least two (2) outside air changes per hour, with sufficient within-room air distribution to dilute or remove tuberculosis bacilli from locations where healthcare facility personnel or visitors are likely to be exposed. ASHRAE recommends that emergency rooms, waiting rooms, and the like have at least ten (10) air changes per hour. The recommended air changes for trauma rooms are twelve (12) air changes per hour, five (5) of which should be outside air. The LEGI-SLATE Report for the Federal Register, L-S ID Number 471062 (4506 lines), Page: 58 FR 52810 NO. 195, dated Oct. 12, 1993, by the Department of Health and Human Services, Centers for Disease Control and Prevention provides a draft of guidelines for preventing the transmission of tuberculosis in health care facilities. Table S3-1 of that report shows how many air changes per hour and time in minutes are required for removal efficiencies of 90%, 99% or 99.9% of airborne contaminants. That report states that with 6 air changes/hour, it takes 69 minutes to reach a 99.97% removal efficiency; at 10 air changes/hour, it takes 41 minutes to reach a 99.97% removal efficiency; and at 20 air changes/hour, it takes 21 minutes to reach a 99.97% removal efficiency.

The updated Table B.1. below, revised by the CDC, substitutes the Table S3-1 of the report.

TABLE B.1

Air changes/hour (ACH) and time required for airborne-contaminant removal by efficiency*

| ACH | Mins. Req for Removal 99% Efficiency | Mins. Req for Removal 99.8% efficiency |
| --- | --- | --- |
| 2 | 138 | 207 |
| 4 | 69 | 104 |
| 6 | 46 | 69 |
| 8 | 35 | 52 |
| 10 | 28 | 41 |
| 12 | 23 | 35 |
| 15 | 18 | 28 |
| 20 | 14 | 21 |
| 50 | 6 | 8 |

*This table is revised from Table S3-1 in reference 4, and has been adapted from the formula for the rate of purging airborne contaminants.

The particular embodiments of the present invention are designed to achieve up to 20 air changes per hour for a typical room installation.

As can bee appreciated, power consumption, unit noise and room size, and hence volume of air to be filtered, are all design factors to be considered in choosing a particular fan for a particular size unit. For example, to provide 10 room air changes per hour in a room having a 15 by 20 floor area and an 8 foot ceiling (2,400 cubic feet volume), it would require moving 400 cubic feet per minute (cfm) of air for one (1) hour, or sixty (60) minutes.

Several descriptions, illustrations and examples have been given to aid in understanding the present invention. One with skill in the art will realize that numerous changes and variations may be made without departing from the spirit of the invention. Each of these changes and variations is within the scope of the present invention.

I claim:

1. An air purification system comprising:
   a high voltage corona discharge chamber having a discharge electrode and collector electrode fluidly coupled to an air inlet port the high voltage corona discharge chamber being powered by a first high voltage power supply;
   a high voltage linear electric field chamber fluidly coupled to the corona discharge chamber, the linear electric field chamber containing an outer first electrode, and a concentric porous barrier filter second electrode; the high voltage linear electric field chamber having a hollow interior constructed to allow air to flow from the linear electric field chamber through the porous barrier filter second electrode and into the hollow interior, the high voltage linear electric field chamber being powered by a second high voltage power supply;
   an ultra-violet (UV) light chamber fluidly coupled to the hollow interior of the porous barrier filter second electrode, the UV light chamber including at least one UV light source;
   an activated charcoal filter constructed to pass air from the UV light chamber to an exit port through an exhaust fan;
   wherein, the fan draws ambient air through the corona discharge chamber, through the high voltage linear electric field chamber, through the porous barrier filter second electrode, through the UV light chamber, through the charcoal filter and into the exit port.

2. The air purification system of claim 1 wherein the corona discharge chamber and the linear electric field chambers are cylindrical.

3. The air purification system of claim 1 wherein the system will pass at least 400 cfm of air from the inlet port to the exhaust port.

4. The air purification system of claim 1 further comprising a wheeled housing.

5. The air purification system of claim 1 wherein the UV chamber includes a UV reflective material.

6. The air purification system of claim 1 wherein the UV light chamber includes a plurality of UV sources.

7. The air purification system of claim 1 wherein the at least one UV light source is a mercury vapor discharge light source.

8. The air purification system of claim 1 wherein the at least on UV light source is an LED.

9. The air purification system of claim 1 wherein the system is powered by AC line voltage.

10. The air purification system of claim 1 wherein the system is powered by batteries.

11. An air purification system comprising a fan configured to draw ambient room air through a high voltage corona discharge region powered by a first power source and subsequently through a high voltage linear electric field filter that has a first solid electrode and a second porous electrode, wherein the room air is passed through the second porous electrode; the high voltage linear electric field filter being powered by a second power source; the fan also configured to draw the room air from the linear electric field filter through an ultra-violet (UV) light region and an activated charcoal filter.

12. The air purification system of claim 11 wherein the corona discharge region is a cylindrical corona discharge chamber.

13. The air purification system of claim 11 wherein the linear electric field filter is a cylindrical chamber that includes the first solid electrode and concentrically the second porous electrode.

14. The air purification system of claim 13 wherein the second porous electrode has hollow interior region, and wherein the room air passes through the porous second electrode into the hollow interior region.

15. A method of purifying air from a room comprising:
   drawing the air from a room through a corona discharge region;
   drawing the air through a linear electric field region, the linear electric field region having at least one porous electrode;
   passing the air through the porous electrode;
   drawing the air through an ultra-violet (UV) light beam;
   expelling the air back into the room;
      wherein the linear electric field region comprises outer and inner concentric conductive cylinders, the outer conductive cylinder being solid, and the inner conductive cylinder being porous, wherein the outer and inner conductive cylinders form electrodes configured to produce a linear electric field.

16. The method of claim 15 wherein the corona discharge region is contained in a high voltage corona discharge chamber.

17. The method of claim 15 wherein said room air is passed through a charcoal filter prior to being expelled back into the room.

18. An air purification system comprising:
(a) an electrostatic barrier filter (EBF) comprising:
  (i) a high voltage corona discharge chamber having a discharge electrode and collector electrode fluidly coupled to an air inlet port;
  (ii) a high voltage linear electric field chamber fluidly coupled to the corona discharge chamber, the linear electric field chamber containing a conductive porous barrier filter element having a hollow interior constructed to allow air to flow from the linear electric field chamber through the conductive porous barrier filter element and into the hollow interior;
(b) a germicidal section comprising:
  an ultra-violet (UV) light chamber fluidly coupled to the hollow interior of the porous filter element, the UV light chamber including at least one UV light source;
(c) an activated carbon section comprising:
  an activated charcoal filter constructed to pass air from the UV light chamber to an exit port through an exhaust fan;
  wherein, the fan is configured to draw ambient air from a room through the electrostatic barrier filter, through the germicidal section, and, through the activated carbon section, returning purified air to the room.

* * * * *